United States Patent [19]
Franks

[11] Patent Number: 4,733,555
[45] Date of Patent: Mar. 29, 1988

[54] PRESSURE ENTRY AND TEST SYSTEM

[76] Inventor: Stephen H. Franks, 5 N. Mill St., Hopkinton, Mass. 01748

[21] Appl. No.: 37,600

[22] Filed: Apr. 13, 1987

[51] Int. Cl.$^4$ ............................................. G01M 3/32
[52] U.S. Cl. ......................................... 73/49.3; 73/52
[58] Field of Search ................................... 73/49.3, 52

[56] References Cited

U.S. PATENT DOCUMENTS

| | | | |
|---|---|---|---|
| 900,324 | 10/1908 | Swangren | 73/49.3 |
| 1,539,937 | 6/1925 | Cochrane | 73/52 |
| 2,749,744 | 6/1956 | Doudera, Jr. et al. | 73/52 |
| 4,205,551 | 6/1980 | Clifford et al. | 73/52 |

FOREIGN PATENT DOCUMENTS 1113440 5/1968 United Kingdom ................. 73/49.3

OTHER PUBLICATIONS

Skye, 1520 Series, Open and Closed Package Testing Systems, SKYE Equipment Co., Ltd. (2pp.).
Automatic System Combinations/Closed Package Testers, The ARO Corporation, Buffalo, NY, (3pp.) 6183.
Product literature for leak testers and flexible package seal strength tester of T.M. Electronics, Inc., Worcester, MA.

*Primary Examiner*—Stewart J. Levy
*Assistant Examiner*—Joseph W. Roskos
*Attorney, Agent, or Firm*—Lahive & Cockfield

[57] ABSTRACT

A pressure testing apparatus has a probe with a piercing tip. The probe sealingly engages a special entry port having a mating pressure-coupling body which establishes a sealing connection with the probe before the tip pierces the package. An adhesive sheet flange extends about the body of the entry port and sealingly secures the body to the package. This eliminates the need for external clamping or holding fixtures. In a preferred embodiment the pressure-coupling body is formed of a semi-rigid material and has a tapered through bore for receiving the probe. A face of the body defines a stop which limits the piercing travel of the probe tip. The probe assembly, in one embodiment has inlet and return ports which accommodate a pressure supply inlet line and a pressure sensing return line, respectively. A single piercing tip enters the packaging, with the inlet port located near to the tip end of the probe, and the return port located at a distal end. The interior of the probe thus serves as a pressure buffer chamber, enhancing the stable performance of a microprocessor-polled pressure sensing unit, and preventing obstruction of the return port or of the sensor by package debris. A pressure supplying and sensing system is shown, which operates at positive or negative pressures.

15 Claims, 4 Drawing Figures

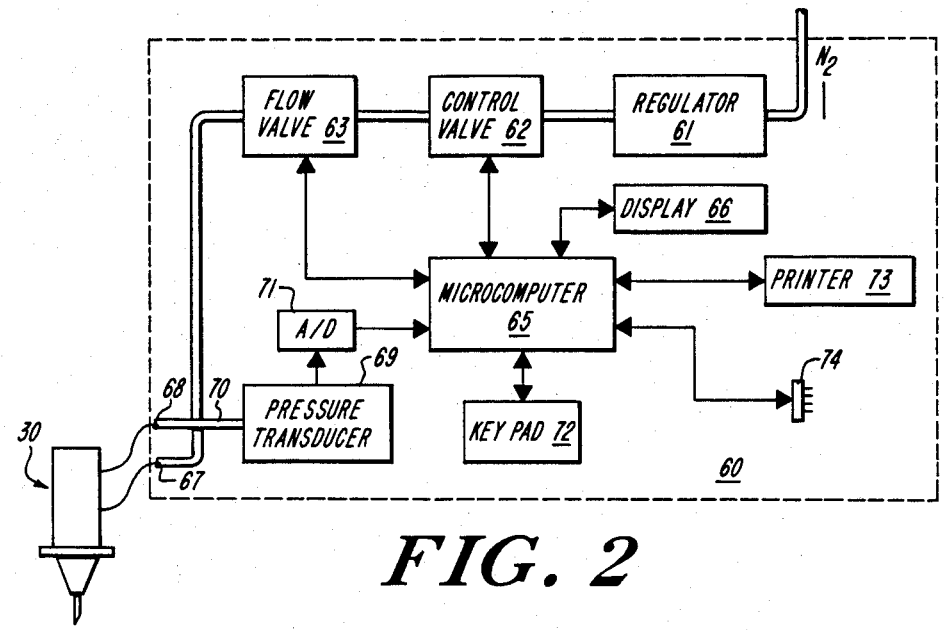
FIG. 2
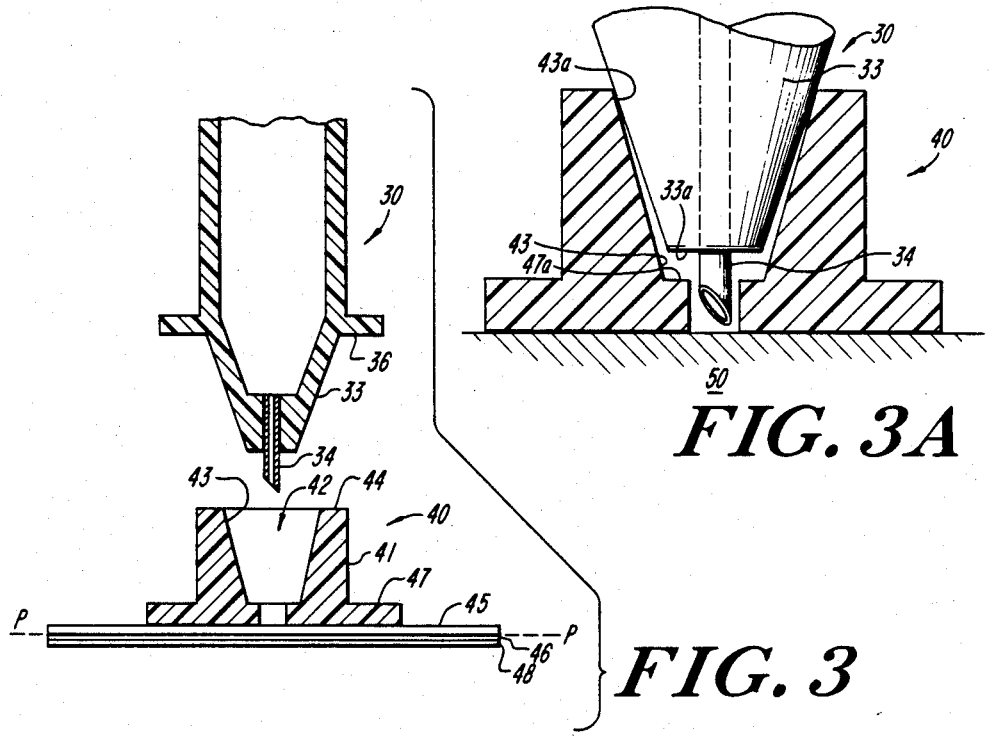
FIG. 3A
FIG. 3

PRESSURE ENTRY AND TEST SYSTEM

BACKGROUND OF THE INVENTION

The present invention relates to apparatus for pressure testing of sealed packages, and particularly to apparatus for burst testing and leakage testing of flexible sealed packages such as used for packaging food products, cosmetics and sterile medical supplies and equipment.

Normal manufacturing quality control protocols require the routine testing of samples of packaged items to assure that production packaging equipment is properly adjusted and operating. For a sealed package such testing may involve pressurizing a package to determine the pressure at which the package bursts, thus providing a measure of seal strength, or may involve pressurizing a package and measuring the rate at which the package leaks, thus providing a measure of seal integrity. In either case, a pressurizing needle or conduit must enter the package to provide pressure, and a second needle or conduit may be required to measure the total internal pressure. Any such conduit must seal against the package.

U.S. Pat. No. 4,205,551 shows one prior art approach to providing entry of a pressure conduit to a sealed package, in which a resilient press member is urged against a package and pressurizing needle to seal the entry point and the lower portion of the package against leakage during testing. The press member, however, may clamp off the upper half of the package, with the result that the device effectively tests only one-half the package. Another prior art device employs a pressure supplying needle surrounded by a suction-cup shaped collar. When the needle penetrates a semi-rigid package, the cup presses against the surrounding package face to seal the area about the needle's entry point. This device is used in connection with a testing jig which urges the assembly against the package and holds it tight during testing.

OBJECTS AND SUMMARY OF THE INVENTION

It is an object of the invention to provide an improved apparatus for the pressure testing of sealed packages.

It is another object of the invention to provide a sealed path between a test apparatus and the interior of a sealed package.

It is another object of the invention to provide a pressure testing apparatus not requiring special jigs or fixtures.

It is another object of the invention to provide a pressure testing apparatus adaptable to testing both inflexible and flexible sheet packaging.

These and other desirable properties are obtained in a pressure testing apparatus having a continuously monitored pressure supply conduit which enters a package with a piercing probe tip. The tip sealingly engages an entry port having a pressure-coupling body which mates with the tip. An adhesive sheet flange extends about the body and seals the body to a package. In a preferred embodiment the pressure-coupling body is formed of a semi-rigid material and has a tapered through bore for receiving the probe. A face of the body defines a stop which limits the piercing travel of the probe tip.

In one embodiment, the probe tip assembly has inlet and return ports which accommodate a pressure supply inlet line and a pressure sensing return line, respectively. A single piercing tip enters the packaging, with the inlet port located near to the tip end of the probe, and the return port located at a distal end. The interior of the probe thus serves as a pressure buffer chamber, enhancing the stable performance of a microprocessor-polled sensing unit, and preventing the obstruction of the return port or sensor by package debris.

BRIEF DESCRIPTION OF THE DRAWINGS

These and other features of the invention will be understood with reference to the following description and to the drawings, in which:

FIG. 2 shows a block diagram of the pressure supply and test apparatus of the system of FIG. 1;

FIG. 3 shows a vertical section of the pressure entry device and probe of FIG. 1; and FIG. 3A is a detailed cross section of the probe tip and entry device in a partially engaged position.

DETAILED DESCRIPTION OF THE DRAWINGS

Figure 1:
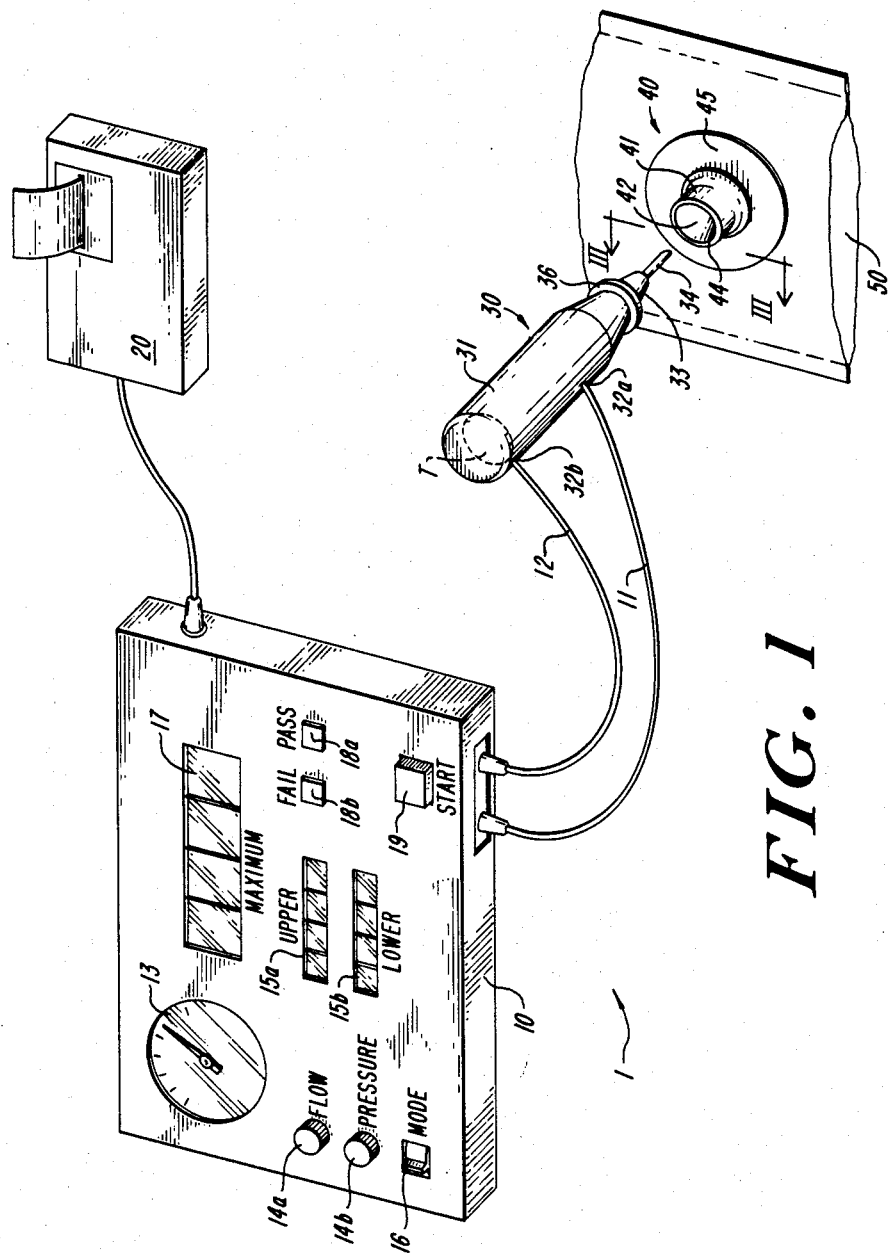
FIG. 1 shows a perspective view of a pressure entry test system according to one embodiment of the invention.

FIG. 1 shows a perspective view of a pressure entry test system 1 for the pressure testing of closed packages. The illustrated system 1 includes a pressure regulating and sensing apparatus 10, a pressure recording device 20, a pressure probe 30, and an adhesive entry port 40. Recording device 20 is a printer which prints a chart or record of test results; the printer is known per se, and is shown to illustrate an output recording, display or storage device generally, for receiving data from test device 10 and creating a record of test results.

The illustrated pressure regulating and sensing apparatus 10 is a general purpose pressure testing apparatus which is configured to perform either leakage or burst testing within a user selectable pressure range, as discussed more fully in relation to FIG. 2 below, and includes for that purpose a number of displays, indicators, adjustment controls and the like, indicated on the panel thereof in FIG. 1.

A pressure-supplying conduit 11 leads from the apparatus to probe 30, and a second pressure-sensing connection 12 returns from the probe to the apparatus 10. It is envisaged that probe 30 may contain an electronic pressure sensing transducer, identified in phantom by "T" in the Figure, in which case connection 12 may be an electrical connection for carrying a pressure indicating electrical signal to apparatus 10. Preferably however, connection 12 is a pressure-tight conduit which places the interior of probe 30 in pressure communication with appropriate sensing devices within apparatus 10. Applicant has found this arrangement particularly advantageous for leak testing, wherein a differential pressure sensor is implemented within apparatus 10.

The other illustrated indicators and controls of apparatus 10 include the following: a pressure meter 13 for indicating the pressure supplied to the apparatus; adjusting dials 14a, 14b for setting an inflation flow rate or maximum pressure, respectively; displays 15a, 15b for setting upper and lower set points; a mode select switch 16 for selecting leakage, burst or pressure entry modes, a display 17 for displaying the measured burst pressure or leakage parameter; a pair of pass/fail indicator lights 18a, 18b; and a start button 19 for initiating a test cycle.

The probe 30 has a probe body 31 with pressure inlet port 32a and return connection 32b, a shoulder 36, a shank portion 33 and a penetrating inflation tip 34. As shown, inflation tip 34 consists of a single hollow needle having a sharp tip cut at an acute angle for piercing a package and for supplying pressure thereto. A double needle, with a pressure-supplying needle coaxially mounted within, or about, a pressure sensing tube tip may also be used. As discussed more fully below, shank 33 is preferably tapered.

Probe 30 sealingly couples to an entry device 40 of novel construction which applicant has found obviates the cumbersome package-holding jigs and press frame structures of the prior art. Entry device 40 has a body portion 41 with a tip rim 44 and a central bore 42 defined by a tapered interior wall 43 (shown in FIG. 3). A peripheral apron 45 extends from the body 41 as a surrounding sheet. The undersurface 46 of apron 45 is coated with a surface layer of high-tack contact-type pressure sensitive adhesive for attaching to a package 50, shown in phantom. In one prototype device, the body portion is formed of a semi-rigid polyvinylchloride polymer and has a wall thickness of approximately (0.05) to (0.10) inches; the sheet apron portion 45 is formed of a flexible polymer approximately (0.005) inches thick. The central bore 42 of the prototype has a taper of approximately 0.06, with the corresponding shank portion 33 of the probe having a somewhat steeper taper, e.g., approximately 0.08 so as to sealingly fit within the bore.

FIG. 3A shows a detailed cross-sectional view of the probe tip 33 in an intermediate insertion position being connected to entry device 40, with the difference in tapers exaggerated for purposes of illustration. As shown, the tapered tip 33 and the inner wall 43 of device 40 sealingly contact each other about a band 43a prior to penetration of package 50 by needle 34. This establishes a pressure- (or vacuum-) tight seal with the sensing apparatus before the package is compromised, so that, for example, the test apparatus may obtain accurate measurements of the pressure or vacuum in the sealed package, prior to, or instead of, performing a burst or leakage test. Device 40 is semi-rigid, so that probe 30 firmly engages device 40 upon further motion of the tip into the bore.

Maximum penetration is defined by shoulder 36 of the probe, which seats against rim 44 of the entry device such that the sharpened tip of the probe needle extends approximately (0.25) inches below the plane defined by apron 45 (FIG. 3). Alternatively, a stop may be provided by the surfaces 33a, 47a shown in FIG. 3A.

In use, the entry device 40 is pressed against the surface of a package culled from a production line, so as to adhere thereto. This provides an entry port to the package, which may, for example, be marked with a lot identifier number and saved for later testing. The adhesive contact holds the package skin taut across the lower end of body bore 42 so that when the probe 30 is inserted into bore 42 for testing, tip 34 will pierce the package without requiring either a special frame to secure the package, or a pressure member to seal the entry point of the probe.

FIG. 2 shows a block diagram of a presently preferred pressure testing apparatus 60 for providing the pressure monitoring and control functions described above in relation to apparatus 10. A regulator 61 receives a pressurized source of gas such as dry nitrogen which it passes at a fixed pressure to a servo-controlled pressure valve 62. Microprocessor 65 reads the control valve setting and provides a visual indication, such as a maximum pressure reading, to display 66. A second flow valve 63, may be provided in line 64 which passes the controlled gas flow to an output port 67 for provision to the probe 30 (FIG. 1).

Return or input port 68 receives the return line from probe 30 and connects to a pressure transducer 69 which provides an analog voltage pressure signal output on line 70 representative of the sensed pressure. This pressure signal is digitized by analog to digital converter 71, and the digitized pressure signal is provided to microcomputer 65 which stores, compares or displays the pressure reading in accordance with a selected test program. Desired test programs and pressure parameters are set via a key pad 72. Computer 65 provides test data to printer 73 and to an output RS232 interface port 74, which may be used, for example, to permit the direct entry of test results into an archive of production test results.

The precise test protocols performed by apparatus 60 may include a test to determine package burst pressure, a measurement of the initial package pressure or vacuum, and a test to determine the rate of leakage from a package at a fixed pressure. For the first test, the microcomputer actuates the flow along line 64 and continuously polls the return pressure at input port 68, saving the greatest pressure valve and terminating the test when the pressure either drops or stabilizes below the maximum set pressure. For the pressure leakage test, the microcomputer actuates the control valve to provide a keypad-selected test pressure to output port 67, closing the valve after a time, and recording the initial pressure valve. Processor 65 then periodically polls the transducer output and displays or prints the pressure difference or the leakage rate. The foregoing protocols involve simple valve control, timing and arithmetical calculations, and are readily implemented as a microcomputer instruction set which permits the rapid set up and cycling through a desired test.

FIG. 3 shows a vertical section through the probe tip and entry device 40 of FIG. 1, illustrating details of a presently preferred construction. Tapered shank 33 of the probe has a length dimension substantially equal to the length of entry device 40, so that when shoulder 36 of the probe seats against the top rim 44 of the entry device, substantially the full length of piercing needle 34 extends below the plane denotd P defined by the lower surface of device 40. Sheet apron 45 has a lower surface with an adhesive coating 46, which is covered by release paper 48 until use. A thickened, semi-rigid flange 47 is integrally formed with the body of device 40 and provides a pedestal for orienting the body 41 with respect to the apron 45. Apron 45 may cover the central bore 42 as shown in the figure, in which case insertion of probe tip 34 punches a hole therethrough as it enters the underlying package. Alternatively, the apron may be formed with an aperture aligned with the bore.

Further, apron 45 may be integrally formed with the body 41 of the entry device, by a pressure molding process, and may be formed as a thicker sheet, omitting flange 47. The adhesive coating 46 is applied separately.

Thus, it will be appreciated that the entry device 40 provides a simple adhesive entry port which may be easily affixed to a package and which greatly simplifies the procedure of pressure testing packages of arbitrary shape, requiring only that the package includes one substantially flat or smooth surface region to which the flange or apron may conform. Illustrated probe 30 provides a single needle probe with a buffered pressure area which screens the pressure sensor from debris, and provides, with apparatus 10, a versatile tester for diverse pressure measurements and test protocols.

It will be appreciated that the foregoing description of the illustrated preferred embodiment is by way of illustration and not of limitation, and that the invention includes other embodiments. The invention being thus disclosed, further variations and modifications will occur to those skilled in the art, and all such variations and modifications are included within the spirit and scope of the invention, as defined by the following claims.

What is claimed is:

1. An improved system for the pressure testing of a sealed package, such system comprising
   a pressure monitoring pressure unit including a probe with an end connector, and
   an entry device for establishing pressure-tight communication between the pressure unit and a sealed package, wherein the entry device comprises
   (i) a connector body adapted to sealingly couple with said end connector, and
   (ii) a package engaging portion extending from said connector body and having a face with an adhesive coating thereon for sealingly adhering to said package so as to affix the entry device in a pressure-tight manner thereto.

2. A system according to claim 1, wherein the probe comprises a pressure inlet and a pressure return port for connection to pressure providing and pressure sensing lines respectively, said probe further having a piercing inflation needle extending therefrom at an end of the probe distal to said return port.

3. A system according to claim 1 wherein said connector body comprises an elongate semi-rigid portion with a central bore therethrough, and a tapered wall portion of said bore for sealingly engaging the end connector.

4. A system according to claim 3, wherein said tapered wall defines said central bore, and further wherein said connector body comprises a flange for orienting said body with said sheet portion across said bore.

5. A system according to claim 1, wherein the pressurizing probe comprises a pressure sensing transducer for developing an electrical signal indicative of pressure in the sealed package.

6. An entry device for the pressure testing of a sealed package, such device comprising
   a semi-rigid body portion having a pressure sealable connector end for pressure tight connection to a pressure line, a pressure-sealable entry end for pressure tight connection to a flexible package, and a passage extending through said body portion from said connector end to said entry end, wherein said entry end includes a flexible sheet portion extending peripherally thereabout and having an adhesive layer thereon for adhesively sealingly securing said entry end to the package whereby the entry device is self-securing to a compliant package without any external mechanical holding or clamping fixture.

7. A entry device according to claim 6, wherein the passage includes a tapered bore for sealingly engaging a tapered pressure supply fitting.

8. An entry device according to claim 7 adapted for sealingly engaging a tapered pressure supply fitting having a piercing tip end located on said fitting at a fixed distance from a stop defining face, wherein said semi-rigid body portion has a face for abutting said stop defining face, such that when said device is adhered to a package and engaged to such a supply fitting the piercing tip sealingly penetrates the package by a predetermined distance.

9. An entry device according to claim 7, wherein said body includes a flange portion defining a base plane generally coincident with said flexible sheet portion.

10. An entry device according to claim 7, wherein said tapered bore comprises a tapered sealing face adapted for sealingly mating with a tapered probe at a first insertion position as the probe is inserted, while semi-rigidly deforming to allow further insertion of such probe.

11. An entry port for providing leak-free pressure communication of a piercing probe to a compliant sealed package, such port comprising
    a flange defining a base surface conformable to a surface region of the package and having an adhesive coating thereon for sealingly adhering the entry port to the package so as to establish a leak-free bond therebetween without external clamping structure, and
    a body extending from said flange and having a central bore for passage of the probe therethrough into the sealed package,
    said body having a seal surface extending entirely about said central bore and adapted to sealingly engage the probe whereby the entry port establishes leak-free pressure communication between the probe and the sealed package.

12. An entry port according to claim 11, wherein the seal surface is a tapered surface defining the central bore.

13. An entry port according to claim 12, further comprising a flexible apron of adhesive sheet material extending from and surrounding said flange for compliantly adhering to the package.

14. An entry port according to claim 12, further comprising a cover sheet of release material, for covering said adhesive coating prior to use of the port.

15. An entry port according to claim 12, further comprising a second surface of said body defining a stop for determining depth of insertion of a probe into the central bore.

* * * * *